United States Patent
Meyer et al.

(10) Patent No.: US 9,968,394 B2
(45) Date of Patent: May 15, 2018

(54) INSTRUMENT FOR REMOVING TABS FROM A REDUCTION SCREW

(71) Applicant: Alphatec Spine, Inc., Carlsbad, CA (US)

(72) Inventors: Nathan Meyer, Vista, CA (US); Eller Torres, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days. days.

(21) Appl. No.: 15/170,386

(22) Filed: Jun. 1, 2016

(65) Prior Publication Data

US 2016/0346017 A1 Dec. 1, 2016

Related U.S. Application Data

(60) Provisional application No. 62/169,430, filed on Jun. 1, 2015.

(51) Int. Cl.
*A61B 17/70* (2006.01)
*A61B 17/88* (2006.01)
*A61B 90/00* (2016.01)

(52) U.S. Cl.
CPC ...... *A61B 17/8863* (2013.01); *A61B 17/7074* (2013.01); *A61B 17/7032* (2013.01); *A61B 2090/037* (2016.02)

(58) Field of Classification Search
CPC ................ A61B 17/70–17/7046; A61B 17/7074–17/7092; A61B 17/8863
See application file for complete search history.

(56) References Cited

U.S. PATENT DOCUMENTS

| | | | |
|---|---|---|---|
| 7,090,679 B2* | 8/2006 | Saint-Martin | A61B 17/7032 606/99 |
| 2005/0171540 A1* | 8/2005 | Lim | A61B 17/7005 606/86 A |
| 2007/0106123 A1* | 5/2007 | Gorek | A61B 1/32 600/210 |
| 2007/0233155 A1* | 10/2007 | Lovell | A61B 17/7076 606/104 |
| 2008/0077138 A1* | 3/2008 | Cohen | A61B 17/708 606/86 A |
| 2008/0125788 A1* | 5/2008 | Cohen | A61B 17/7085 606/104 |
| 2008/0221626 A1* | 9/2008 | Butters | A61B 17/7086 606/86 A |

(Continued)

*Primary Examiner* — Jan Christopher Merene
*Assistant Examiner* — Steven Cotroneo
(74) *Attorney, Agent, or Firm* — Dinsmore & Shohl LLP

(57) ABSTRACT

An instrument for breaking off and retaining the tab of a reduction screw is provided. The instrument includes a breaking arm and a retaining mechanism. The breaking arm is configured to break off an excess portion of the tab of the reduction screw about a weakened section. The retaining mechanism is configured to retain the broken off tab and preventing the tab from falling into a surgical site. The retaining mechanism is further configured to allow the instrument to engage another tab while simultaneously holding a predetermined number of previously broken off tabs. Accordingly, the instrument reduces surgical time as the surgeon may simply move from one reduction screw to another while breaking off the tabs until the instrument can no longer retain additional broken off tabs.

18 Claims, 9 Drawing Sheets

(56) References Cited

U.S. PATENT DOCUMENTS

| | | | |
|---|---|---|---|
| 2008/0262318 A1* | 10/2008 | Gorek | A61B 17/0206 600/235 |
| 2009/0198279 A1* | 8/2009 | Zhang | A61B 17/7023 606/264 |
| 2011/0218581 A1* | 9/2011 | Justis | A61B 17/708 606/86 A |
| 2013/0018419 A1* | 1/2013 | Rezach | A61B 17/7076 606/264 |
| 2015/0066088 A1* | 3/2015 | Brinkman | A61B 17/708 606/264 |
| 2015/0230836 A1* | 8/2015 | Cochran | A61B 17/7086 606/86 A |
| 2016/0113685 A1* | 4/2016 | Ishii | A61B 17/7032 606/266 |

* cited by examiner

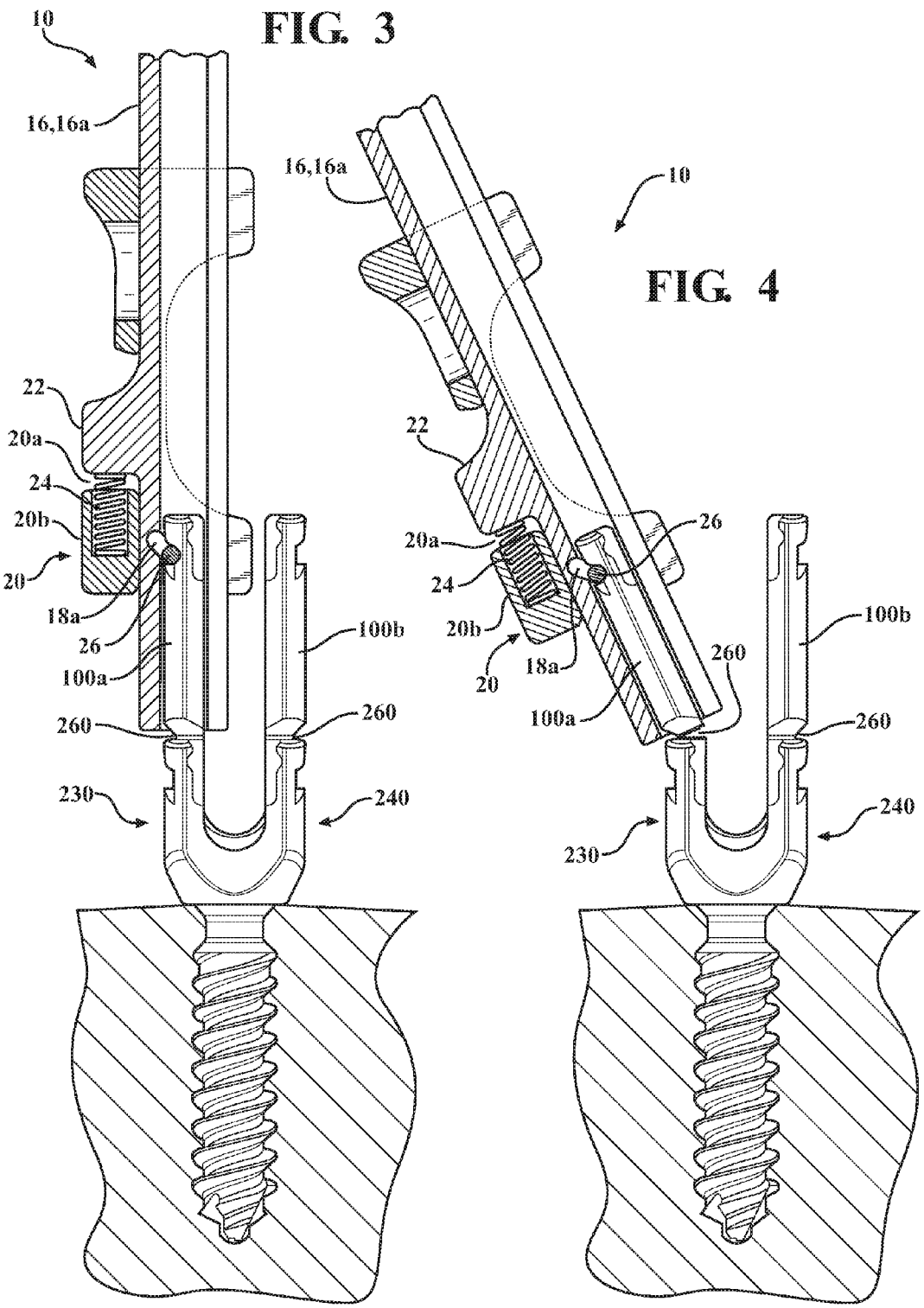

INSTRUMENT FOR REMOVING TABS FROM A REDUCTION SCREW

RELATED APPLICATION

This application claims priority to U.S. Provisional Patent Application Ser. No. 62/169,430 filed Jun. 1, 2016, the entirety of which is incorporated herein by reference.

TECHNICAL FIELD

An instrument configured to remove and retain the tabs of a reduction screw is provided.

BACKGROUND OF THE INVENTION

Reduction screws are used in spinal surgery to help align the spinal column to a rod. Such reduction screws may include a polyaxial body and a threaded member. A pair of spaced apart tabs extend from the polyaxial body and a set screw is threadably engaged between the pair of tabs. The rod is disposed within the space between the set screw and the threaded shaft. Thus, rotation of the set screw pushes the rod and the polyaxial body together.

To accommodate the depth of the surgical site and the length of the screw, the tabs are elongated so as to extend out of the patient's body. It is desirable to have the portion extending beyond the body removed prior to closure of the surgical site. Accordingly, the tabs include at least one weakened section. Generally the weakened section is a thinned-out section of the tab. The thinned-out section runs along a circumference of the tab. Thus, depending on the depth of the surgical site, the length of the tab may vary.

The tab is broken from the polyaxial body along the weakened section prior to closure of the surgical site after reduction of a rod into the screw. Currently this is done by pivoting the free end of a respective tab about the weakened section so as to snap the tab from the polyaxial body. Currently, removing the tabs requires each tab to be broken individually and discarded which increases the surgical time. Accordingly, it remains desirable to have an instrument which is configured to simultaneously remove a tab and also to retain the tabs so as to reduce surgical time and prevent the tabs from falling into the surgical site.

SUMMARY OF THE INVENTION

An instrument for removing tabs from a reduction screw and retaining the tabs is provided. The instrument includes a breaking arm having a retaining mechanism. The breaking arm includes an elongated housing. The elongated housing is configured to receive a tab broken off of the reduction screw. The elongated housing includes an elongated slot on opposite side walls of the elongated housing. The elongated slots are angled with respect to the elongated housing.

The retaining mechanism includes a tab retaining pin. The tab retaining pin transverses the width of the elongated housing and each end of the tab retaining pin is disposed within a respective elongated slot. The retaining mechanism further includes a slide and a biasing member. The slide is attached to the tab retaining pin wherein the biasing member moves the slide and the tab retaining pin into an engaged position, wherein movement of the slide against the biasing member moves the tab retaining pin along respective elongated slots into a disengaged position. In the engaged position, the tab retaining pin is configured to engage a tab within the elongated housing and in the disengaged position the tab retaining pin is moved free of the tab so as to allow the tab(s) to slide out of the elongated housing.

In one embodiment, the instrument includes a pair of breaking arms pivotable about a distal end of a carrier. A drive shaft is fitted through an elongated bore of the carrier. A pair of pivot arms are fixedly mounted to each of the breaking arms and also to the drive shaft. Axial advancement of the drive shaft drives each end of the pivot arm axially forward which in turn rotates the other end of the pivot arm outward so as to radially displace the breaking arms from the carrier and the tabs of the reduction screw are broken along the weakened section. Otherwise stated, the weakened section of the tab serves as a fulcrum for which the breaking arms pivot upon. As the breaking arms pivot, the breaking arms carry with it the respective tab removed about the weakened section.

The instrument may further include a handle disposed on a proximal end of the drive shaft. A proximal end of the drive shaft includes a button protruding from the handle. The button may be depressed so as to advance the drive shaft forward thus urging a first end of the pivot arm forward within the carrier and displacing the other end of the pivot arm outwardly so as to displace the breaking arms radially away from the carrier.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings where like structure is indicated with reference numerals and in which:

FIG. 3 is a cross-sectional view taken along the lines 3-3 of the instrument shown in FIG. 1, showing the instrument engaged with a tab;

FIG. 4 is a view of FIG. 3 showing the instrument breaking a tab;

DETAILED DESCRIPTION OF THE PREFERRED EMBODIMENTS

An instrument for breaking off and retaining the tab of a reduction screw is provided. The instrument includes a breaking arm and a retaining mechanism. The breaking arm is configured to break off an excess portion of the tabs of a reduction screw about a weakened section.

The retaining mechanism is configured to retain the broken off tab, preventing the tab from falling into the surgical site. The retaining mechanism is further configured to allow the instrument to engage another tab while simultaneously holding a predetermined number of tabs. Accordingly, the instrument reduces surgical time as the surgeon may simply move from one reduction screw to another while breaking off the tabs of each reduction screw until the instrument can no longer retain another broken off tab.

In one embodiment, the instrument includes a breaking arm. The breaking arm includes an elongated housing. The elongated housing is configured to receive a tab broken off of the reduction screw. The elongated housing includes an elongated slot on opposite side walls of the elongated housing. The elongated slots are angled with respect to the elongated housing.

In another embodiment, the instrument includes a pair of breaking arms. Each breaking arm is configured to hold a respective tab of a reduction screw and pivot the tab about the weakened section so as to break the tabs off of the reduction screw. The breaking arms may be actuated by a simple push of a button.

Figure 7:
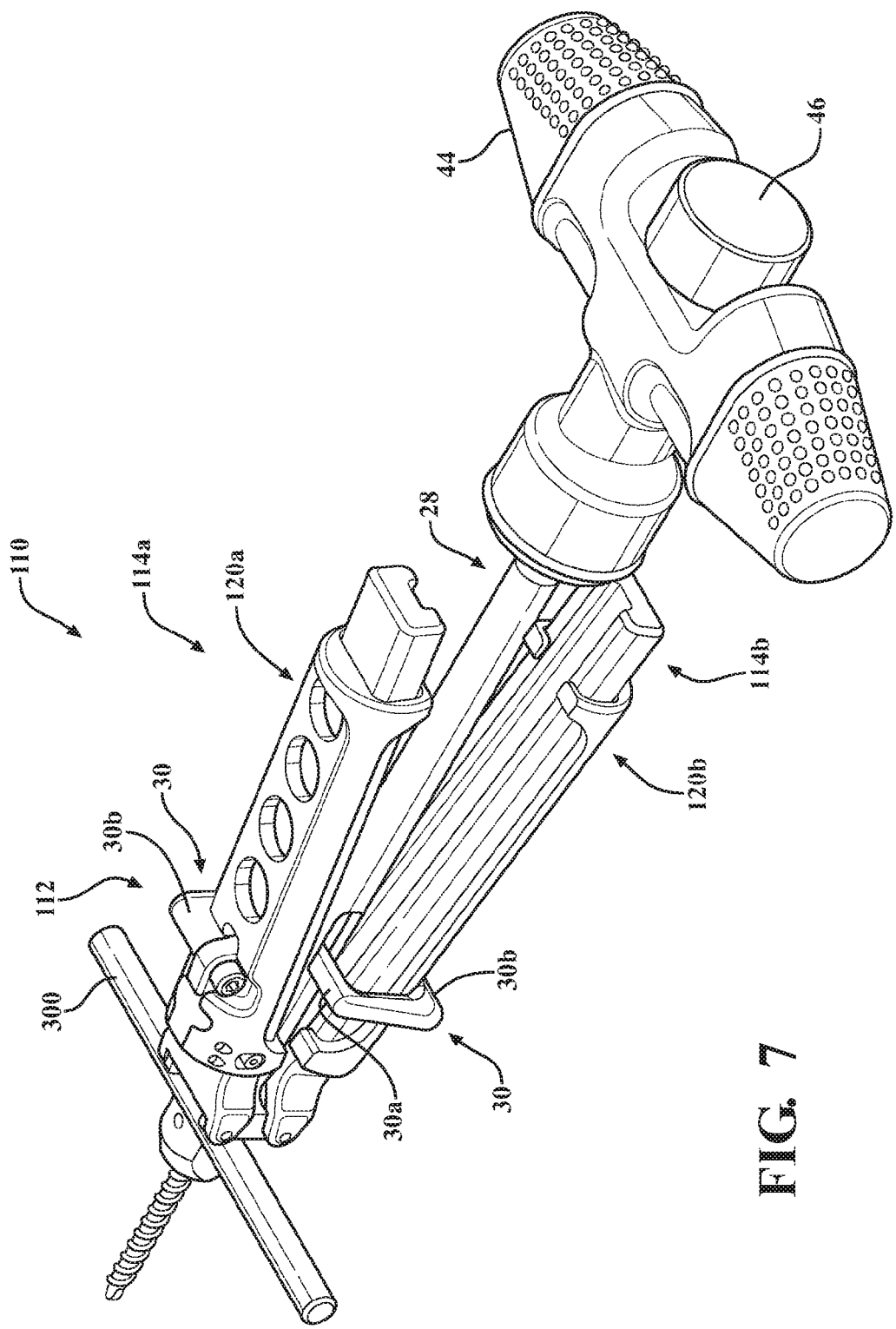
FIG. 7 is perspective view of an instrument for removing and retaining tabs from a reduction screw with two breaking arms according to one or more embodiments described and illustrated herein.
Figure 10C:
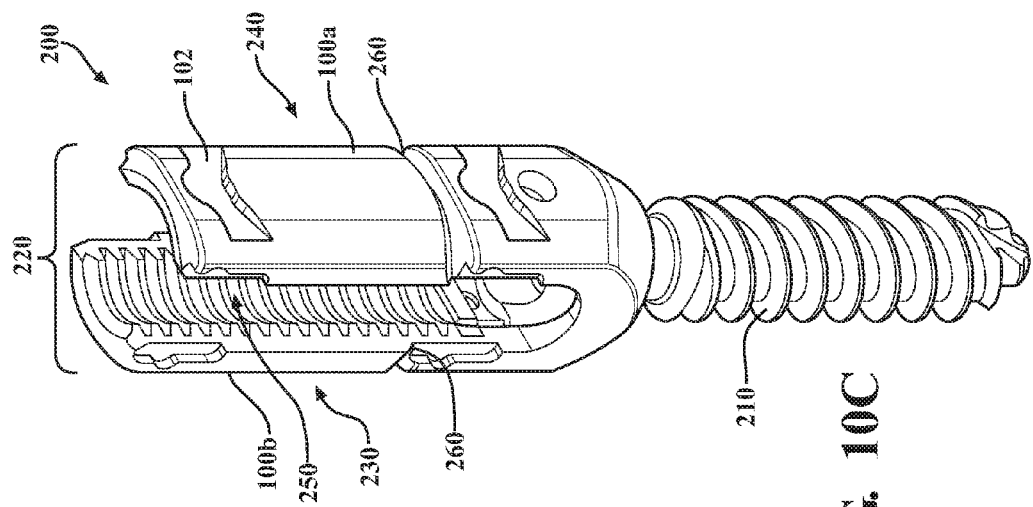
FIG. 10c is a perspective view of the reduction screw showing the threaded inner walls of the tab.
Figure 10B:
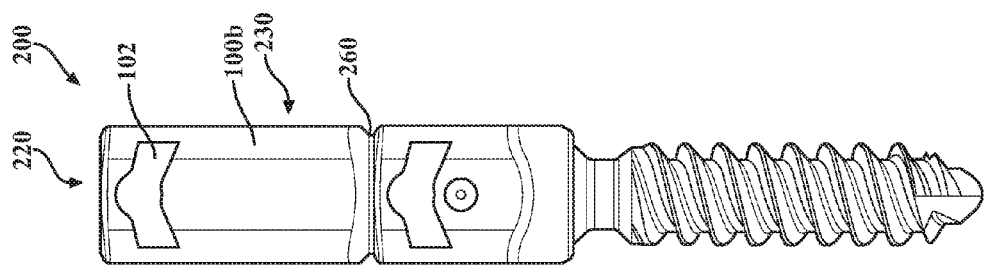
FIG. 10b is side view of the reduction screw shown in FIG. 10a showing the line of weakening.
Figure 10A:
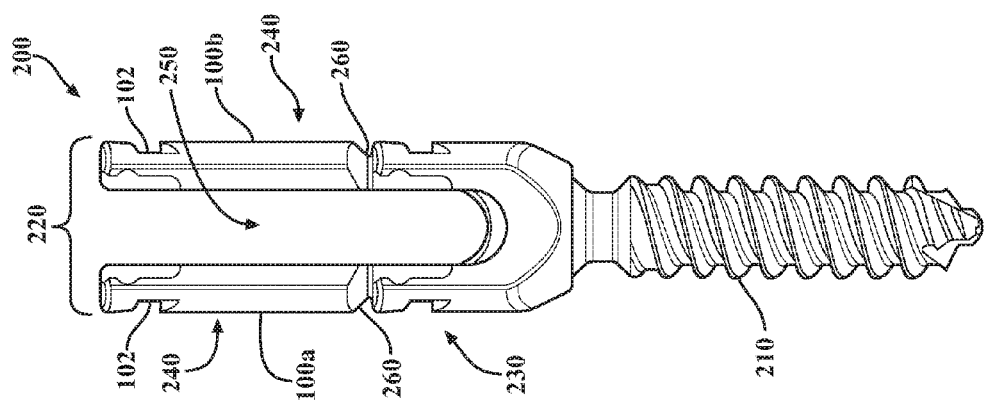
FIG. 10a is a frontal view of a reduction screw showing the pair of tabs spaced apart from each other.

With reference now to FIGS. 10a-10c, an illustrative view of a reduction screw 200 is provided. The reduction screw 200 includes a threaded shaft 210 projecting from a body member 220. The body member 220 includes a first body portion 230 opposite and spaced apart from a second body portion 240 so as to define a slot 250 configured to receive a rod 300 (FIG. 7). The first and second body portions 230, 240 include an indent 260 extending radially along the outer surface of the first and second body portions 230, 240 so as to define a line of weakening (also referred to as a weakened section). The indent 260 separates the first and second body portion 230, 240 from a respective tab 100. Each tab 100 includes a tab indent 102 for engaging with various surgical instruments.

Figure 1:
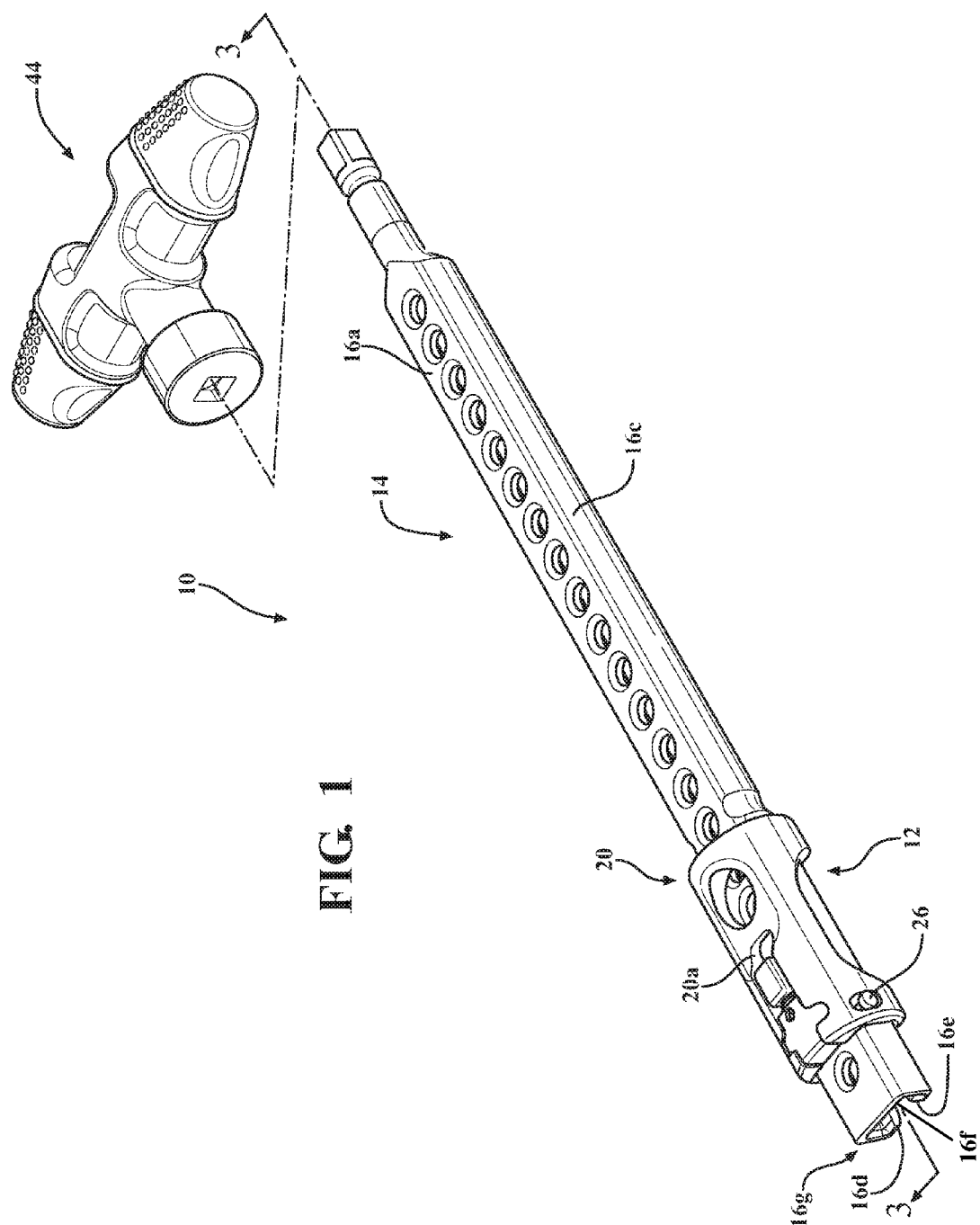
FIG. 1 is a side view of an instrument for removing and retaining tabs from a reduction screw according to one or more embodiments described and illustrated herein.
Figure 2:
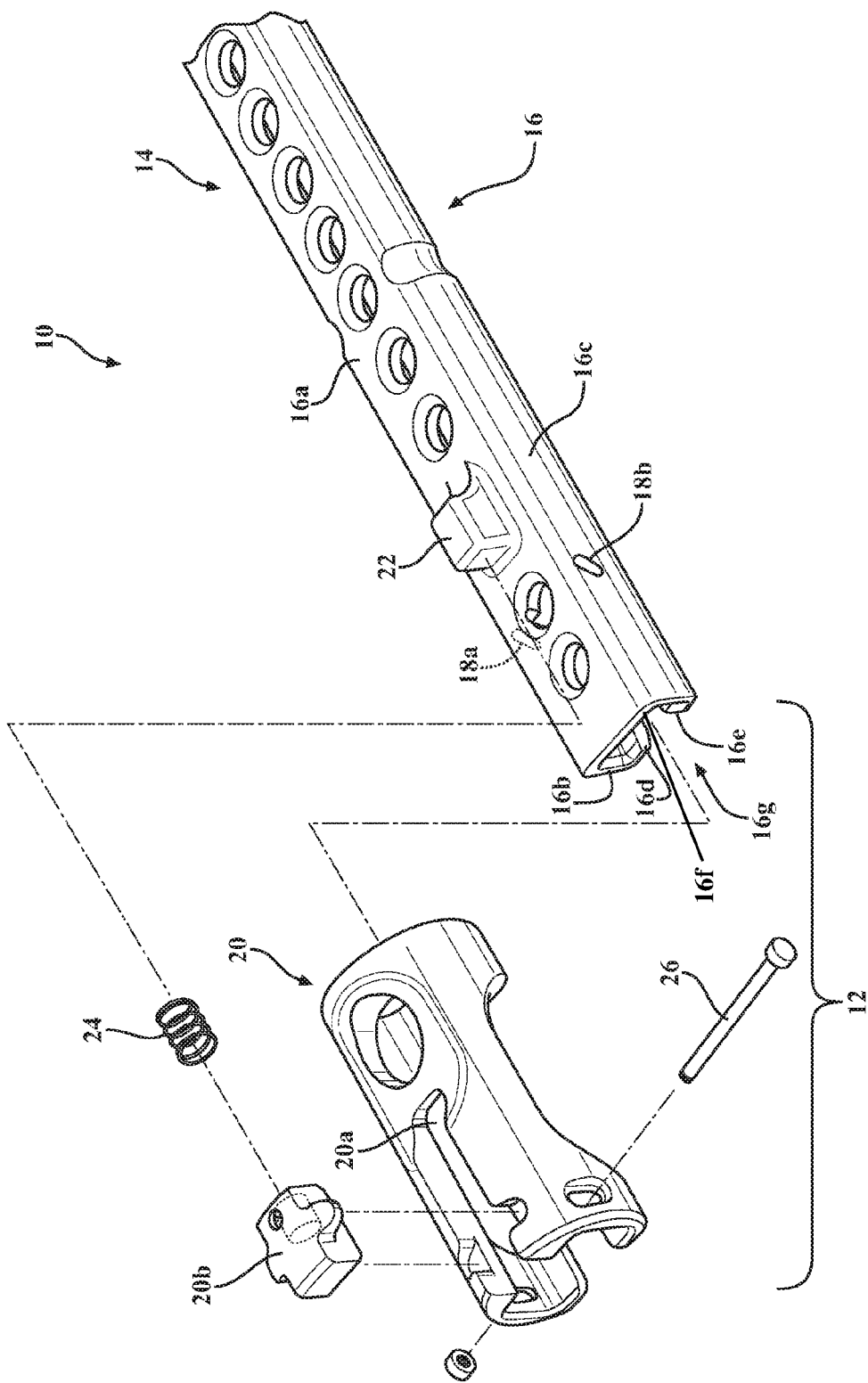
FIG. 2 is an exploded view of the instrument shown in FIG. 1.

With reference now to FIGS. 1-2, an instrument 10 for breaking off and retaining the tabs 100 of the reduction screw 200 is provided. The instrument 10 includes a retaining mechanism 12 and a breaking arm 14. The breaking arm 14 includes an elongated housing 16. The elongated housing 16 is generally defined by a top wall 16a, a back wall 16f, a pair of side walls 16b, 16c, and a pair of inner ledges 16d, 16e extending from the pair of side walls 16b, 16c, respectively, spaced apart from the back wall 16f and extending the length of the breaking arm 14. The elongated housing 16 is configured to receive a respective tab 100 of the reduction screw 200. The back wall 16f is configured to prevent tabs 100 from escaping and the length of the elongated housing 16 defines the number of tabs 100 each breaking arm 14 may retain.

The elongated housing 16 further includes a pair of elongated slots 18a, 18b. Each elongated slot 18a, 18b is opposite the other and disposed on respective side walls 16b, 16c of the elongated housing 16. The elongated slots 18a, 18b are angled with respect to the elongated housing 16. In one embodiment, the elongated slots 18a, 18b are angled so as to slant downwardly from the proximal end of the elongated housing towards a working end 16g of the elongated housing 16.

The retaining mechanism 12 includes a slide 20. The slide 20 is slidably mounted to the top wall 16a adjacent the working end 16g of the elongated housing 16. The working end 16g of the elongated housing 16 is open so as to receive a tab 100 between the back wall 16f and the pair of inner ledges 16d, 16e. The slide 20 includes a block member opening 20a. A block member 22 is formed on the top wall 16a of the elongated housing 16, is fixedly mounted to the top wall 16a and disposed within the block member opening 20a of the slide 20. A first biasing member 24 is positioned relative to the block member 22 and the slide 20 so as to urge the slide 20 towards the working end 16g of the elongated housing 16. In one embodiment, the slide 20 may include a spring support 20b. The spring support 20b is fixedly mounted to the slide 20. The first biasing member 24 pushes against the spring support 20b advancing the slide 20 towards the working end 16g of the elongated housing 16.

The retaining mechanism 12 further includes a tab retaining pin 26. The tab retaining pin 26 transverses the width of the elongated housing 16 and rides within the elongated slots 18a, 18b. The slide 20 is attached to the tab retaining pin 26 and the first biasing member 24 is configured to urge the slide 20 towards the working end 16g of the elongated housing 16 so as to move the tab retaining pin 26 into an engaged position. Movement of the slide 20 against the first biasing member 24 and away from the working end 16g of the elongated housing 16 moves the tab retaining pin 26 along the respective elongated slots 18a, 18b into a disengaged position. In the engaged position, the tab retaining pin 26 is configured to engage a tab 100 within the elongated housing 16 and in the disengaged position, the tab retaining pin 26 is moved free of the tab 100 so as to allow the tab(s) to slide out through the opening of the working end 16g of the elongated housing 16. Stated differently, in the engaged position the tab retaining pin 26 is positioned within the elongated slots 18a, 18b towards the working end 16g and thereby blocks the retained tab(s) 100 in the elongated housing 16 from sliding towards the working end 16g. In the disengaged position the tab retaining pin 26 is positioned within the elongated slots 18a, 18b towards the proximal end the elongated housing 16 and thereby allows the retained tab(s) 100 in the elongated housing 16 to slide towards and out the working end 16g.

With reference now to FIGS. 3-6 a description of the operation of the instrument 10 is provided. The instrument 10 is shown breaking off tabs 100a, 100b from respective first and second body portions 230, 240 of the reduction screw. FIG. 3 shows a cross-sectional view of the instrument 10 engaged with the tab 100a of a reduction screw 200. The tab 100a is disposed within the elongated housing 16, held therein between the back wall 16f, inner ledges 16d, 16e and side walls 16b, 16c. The tab 100a is shown seated within the elongated housing 16 and the tab retaining pin 26 is engaged with the tab indent 102. FIG. 3 illustrates how the tab retaining mechanism 12 operates to hold a tab 100a within the elongated housing 16. In particular, the first biasing member 24 urges the slide 20 towards the working end 16g of the elongated housing 16. The slide 20 carries and pushes the tab retaining pin 26 into the engaged position, wherein the tab retaining pin 26 is spaced apart from the inner surface of the back wall 16f and pinches against the tab 100a.

FIG. 4 illustrates how the tab 100a is broken off of the reduction screw 200. In particular, the breaking arm 14 is pivoted snapping the tab 100a off of the first body portion 230 of the reduction screw 200 about the indent 260. FIG. 4 illustrates the broken off tab 100a being retained within the elongated housing 16 by the tab retaining mechanism 12 as described above.

Figure 5:
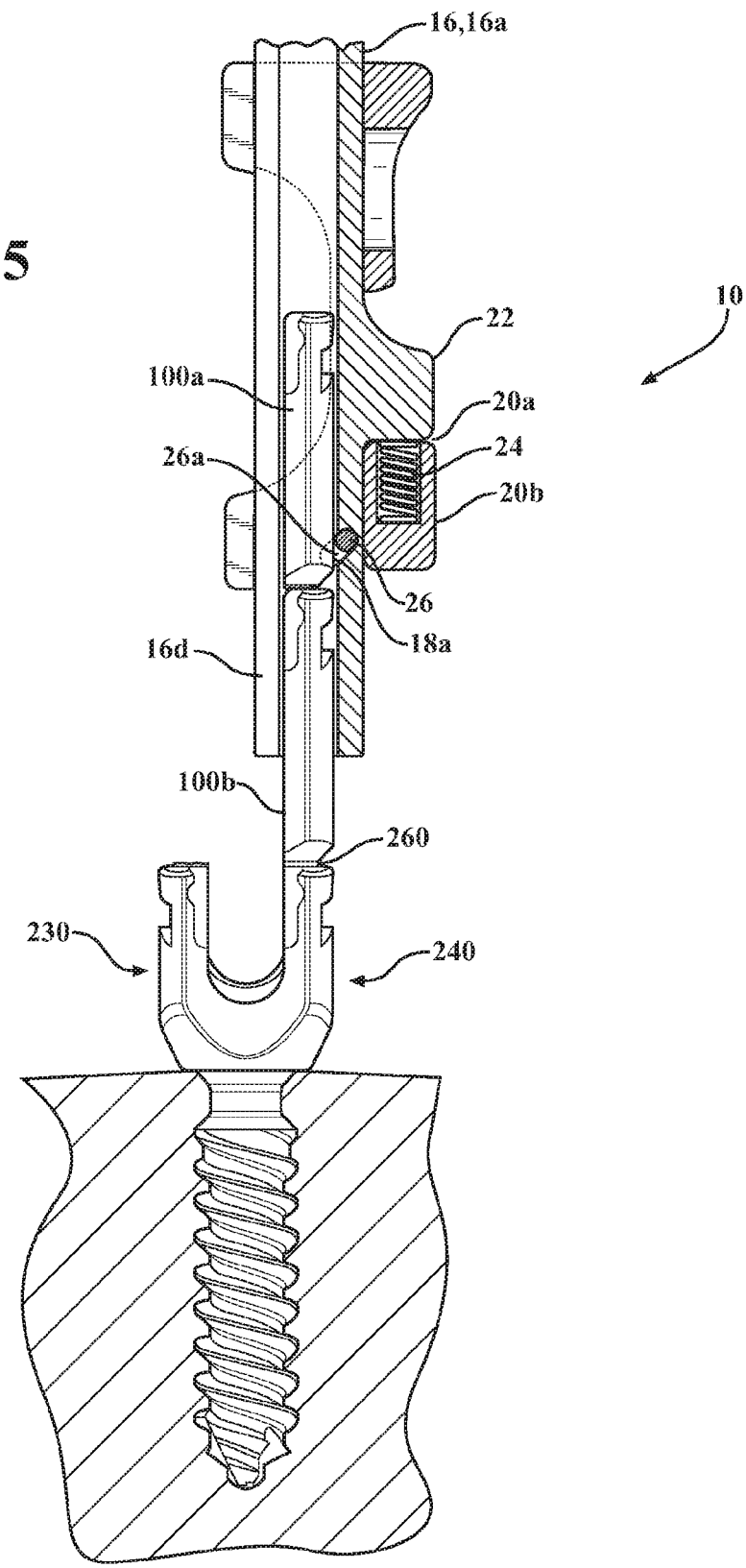
FIG. 5 is a view of FIG. 4 showing the instrument engaging a second tab.

FIG. 5 illustrates the instrument 10 being used on a remaining tab 100b. The first tab 100a is retained within the elongated housing 16 and pushed towards the proximal end of the instrument 10 so as to make way for the second tab 100b. As the first tab 100a is pushed up, the tab 100a urges the tab retaining pin 26 upwardly into respective elongated slots 18a, 18b towards the back wall 16f of the elongated housing 16. FIG. 5 also illustrates how the slide 20 may be pulled against the first biasing member 24 towards the block member 22 so as to position the tab retaining pin 26 into an upper portion of the elongated slot 18a, 18b. In particular, the back wall 16f of the elongated housing 16 includes a pin housing 26a. The pin housing 26a is generally an elongated slot disposed on the back wall 16f transversing the width of the breaking arm 14. The slide 20 is configured to push the tab retaining pin 26 into the pin housing 26a when pulled proximally so as to position the tab retaining pin 26 clear of the tab 100. The pin housing 26a is in open communication with a proximal end of the elongated slots 18a, 18b.

Figure 6:
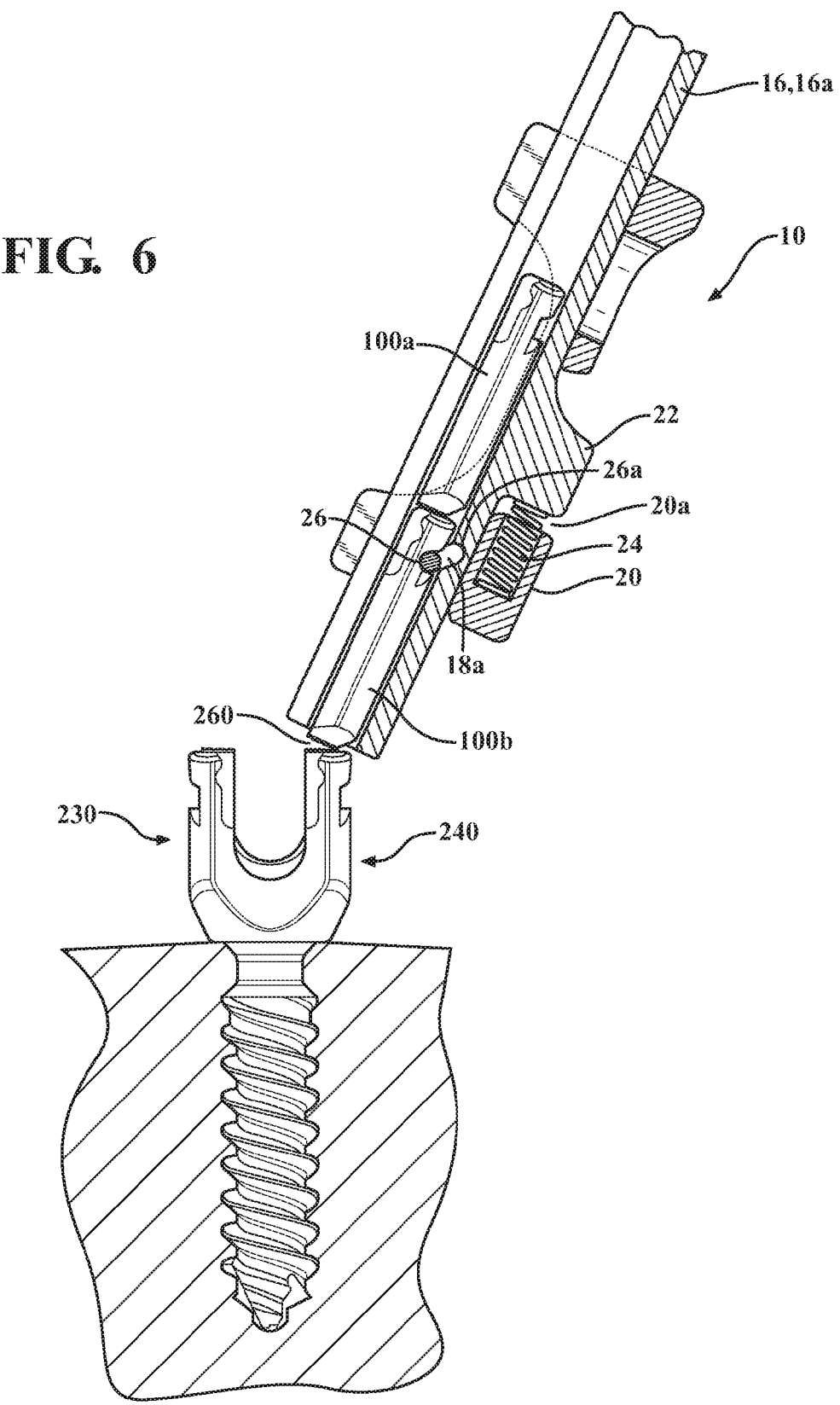
FIG. 6 is a view of FIG. 5 showing the instrument holding two tabs.

FIG. 6. illustrates the instrument 10 being used to break off the remaining tab 100b. The working end 16g of the instrument 10 is adjacent the indent 260. The tab indent 102 of tab 100b is engaged with the tab retaining pin 26. It should be appreciated that when the instrument 10 is clear of the reduction screw 200, the tabs 100a, 100b are retained in the elongated housing 16. In particular, tab 100b is pinched against the inner ledges 16d, 16e by the tab retaining pin 26 and tab 100b supports tab 100a within the elongated housing 16. Releasing the tabs 100a, 100b may be done by simply pulling the slide 20 towards the proximal end of the instrument 10 which pulls the tab retaining pin 26 up the elongated slots 18a, 18b towards the back wall 16f so as to place the tab retaining pin 26 clear of the tabs 100a, 100b (as shown in FIG. 5) and allowing tabs 100a, 100b to slide out the working end 16g of the instrument 10.

Figure 8:
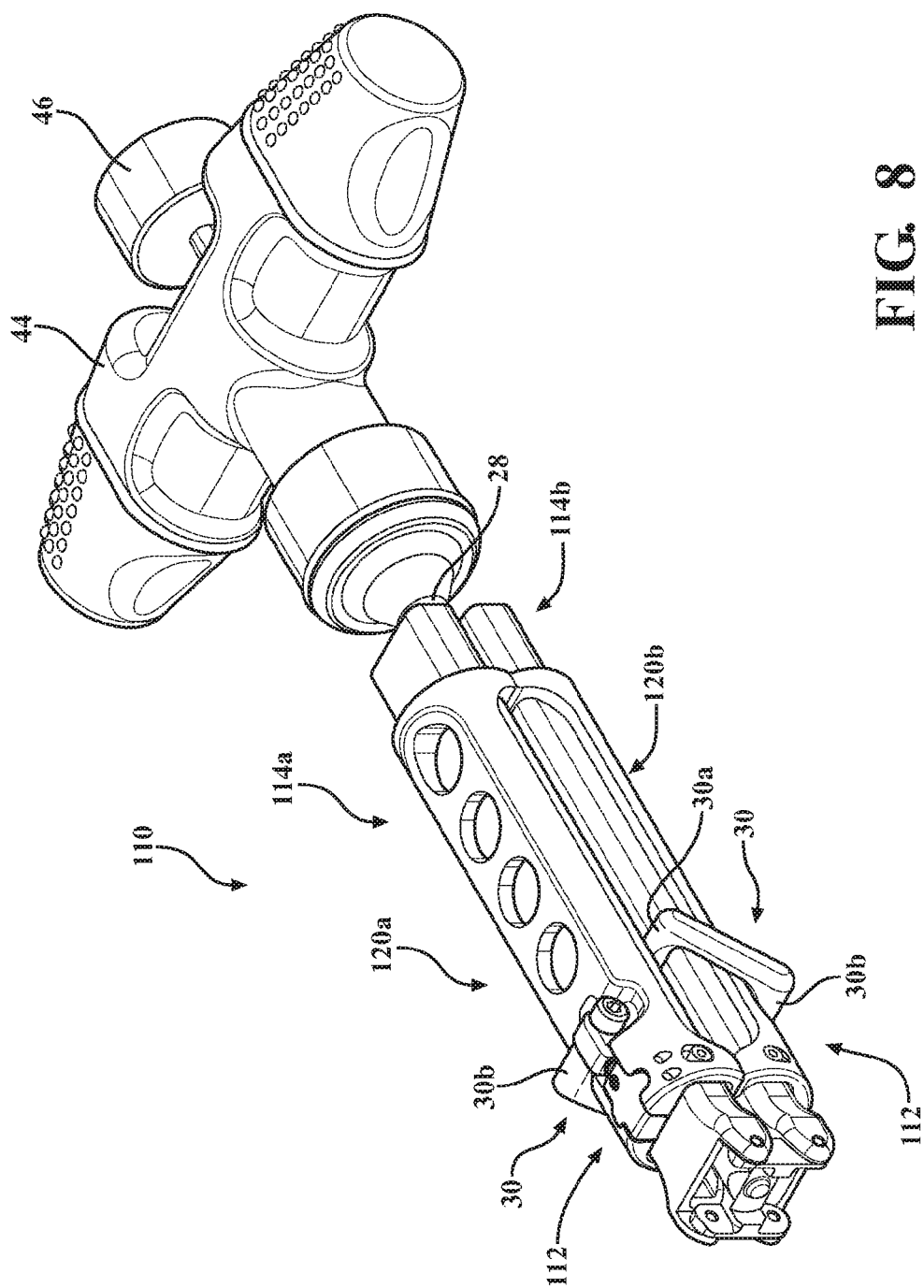
FIG. 8 is a perspective view of the instrument shown in FIG. 7 with the breaking arms closed.
Figure 9:
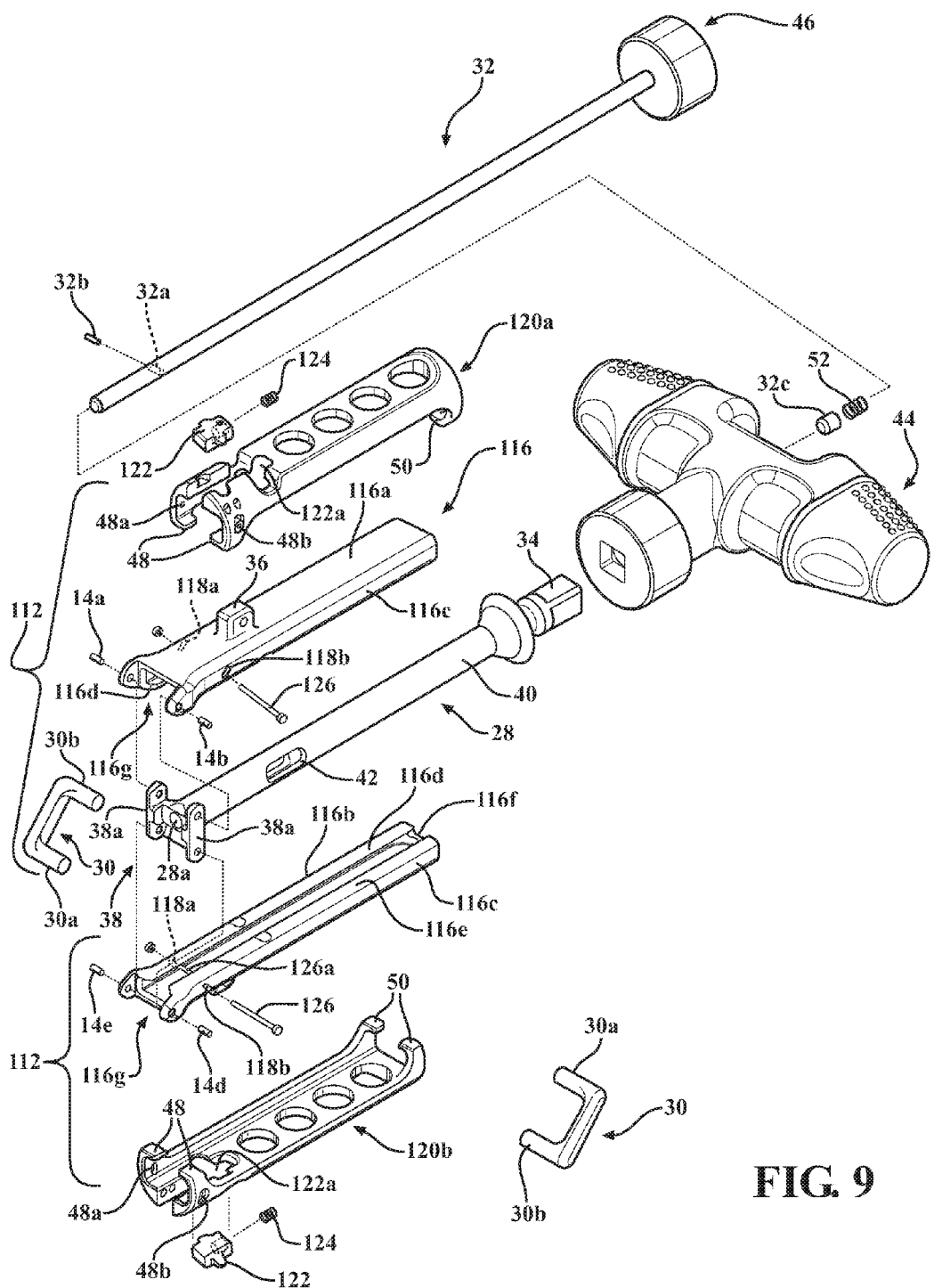
FIG. 9 is an exploded view of the instrument shown in FIG. 7.

With reference now to FIGS. 7-9 a second embodiment of an instrument for breaking off and retaining the tabs of a reduction screw is provided wherein like elements are referenced by like numbers increased by 100. The instrument 110 includes a retaining mechanism 112 and a pair of breaking arms 114a, 114b. The first breaking arm 114a and the second breaking arm 114b are configured to be radially displaced from each other. The breaking arms 114a, 114b each include an elongated housing 116 configured to receive a respective tab 100 of the reduction screw 200. The distal ends of the breaking arms 114 are pivotally mounted to a carrier 28.

The retaining mechanism 112 further includes a pair of pivoting arms 30. Each pair of pivoting arms 30 includes a first arm 30a and a second arm 30b. The first arm 30a of each of the pair of pivoting arms 30 is rotatably mounted to a drive shaft 32. The second arm 30b of each of the pair of pivoting arms 30 is rotatably mounted to a respective first breaking arm 114a and second breaking arm 114b.

Each elongated housing 116 is generally defined by a top wall 116a, a back wall 116f, a pair of side walls 116b, 116c, and a pair of inner ledges 116d, 116e extending the length of the respective breaking arms 114a, 114b. Each elongated housing 116 has a working end 116g and is configured to receive a respective tab 100 of the reduction screw 200. The elongated housings 116 further include a pair of elongated slots 118a, 118b. Each elongated slot 118a, 118b is opposite the other and disposed on respective side walls 116ab, 116c of the elongated housing 116. The elongated slots 118a, 118b are angled with respect to the elongated housing 116. In one embodiment, the elongated slots 118a, 118b are angled so as to slant downwardly from the proximal end of the elongated housing towards the working end 116g and away from the back wall 116f.

The back wall 116f is configured to prevent tabs 100 from escaping. The length of the breaking arms 114a, 114b defines the number of tabs 100 each breaking arm 114a, 114b may retain. The breaking arms 114a, 114b include a pivot support structure 36. Each pivot support structure 36 is fixedly formed to the top wall 116a of a respective breaking arm 114a, 114b.

FIG. 9 provides an isolated view of the carrier 28. The carrier 28 includes an engagement end 34 opposite a support head 38. The support head 38 includes a pair of support members 38a, 38b. The support members 38a, 38b are generally elongated members. Each end of the support members 38a, 38b have a distal end with a pin aperture for pivotally receiving a distal end of a respective breaking arm 114a, 114b (as shown in FIGS. 8 and 9). The pin apertures are located adjacent the line of weakening/indent 260 of the tab 100 when a tab 100 is inserted into a respective breaking arm 114a, 114b between the back wall 116f and the inner ledges 116d, 116e. Support pins 14a, 14b, 14c and 14d are coupled to the pin apertures at each end of the support members 38a, 38b and the distal end of the breaking arms 114a, 114b so as to allow the distal ends of the breaking arms 114a, 114b to pivot about the support members 38a, 38b and the support head 38.

The carrier 28 includes an elongated shaft 40 having a through hole 28a for which the drive shaft 32 is slidably mounted. The carrier 28 includes a first slot 42. The first slot 42 has a length extending along the axial length of the elongated shaft 40.

The drive shaft 32 includes a pin aperture 32a. A drive shaft pin 32b is mounted within the pin aperture 32a and is dimensioned to extend beyond the outer surface of the drive shaft 32 and engage respective first arms 30a of the pair of pivoting arms 30. The drive shaft 32 is slidably mounted within the through hole 28a of the carrier 28. The axial displacement of the drive shaft 32 is limited to the length of the first slot 42 by engagement of the drive shaft pin 32b. The drive shaft 32 further includes a second biasing member 52 and a head portion 32c. The second biasing member 52 is disposed on a distal end of the drive shaft 32 and urges the head portion 32c distally.

The instrument 110 includes a handle 44 and a button 46. The button 46 protrudes from the handle 44. Actuation of the button 46 engages the breaker arms 114a, 114b. In particular, actuation of the button 46 axially advances the drive shaft 32 in a distal direction. The drive shaft 32 cooperates with the first arm 30a of the pivoting arms 30 which in turn radially displaces the second arm 30b. As the second arm 30b is attached to a respective breaking arm 114,a, 114b the distal ends of the breaking arms 114,a, 114b pivot about the line of weakening/indent 260 of the tabs 100 and break the tabs 100 off of the first and second body portions 230, 240 of the reduction screw 200. Such a breaking position of the breaking arms 114a, 114b is shown in FIG. 7. As shown, the handle 44 may be ribbed or may have tactile gripping features to help steady the instrument 10. The advancement of the drive shaft 32 by the button 46 is limited by the handle 44. Thus, it should be appreciated that the degree of pivot for a respective breaking arm 14 may be engineered based upon the length of advancement of the drive shaft 32 and the length of the pivoting arm 14.

The instrument 110 includes a pair of slides 120a, 120b. Each slide 120a, 120b is slidably mounted to a respective breaking arm 114a, 114b. The slides 120a, 120b may be axially displaced with respect to a respective breaking arm 114a, 114b so as to urge a tab retaining pin 126 into a pin housing 126a thus allowing the broken tab 100 to slide out of the distal end of the elongated housing 116. The slides 120a, 120b include a pair of distal retaining arms 48 opposite a pair of proximal retaining arms 50. The slides 120a, 120b have a generally elongated body extending between the distal and proximal retaining arms 48, 50. The pair of distal retaining arms 48 include a pair of pin apertures 48a, 48b.

Each slide 120a, 120b includes a block member opening 122a. The block member opening 122a is configured to receive a block member 122. The block member 122 may be fixed to the distal retaining arms 48 by pins (not shown) fed through the pin apertures 48a, 48b. A first biasing member 124 is positioned between the block member 122 and the pivot support structure 36. As the block member 122 is fixed to a respective slide 120, it should be appreciated that the first biasing member 124 continuously urges the respective slide 120 towards the working end 116g of the elongated housing 116. Also, the drive shaft 32 is mounted within the carrier 28 and the second biasing member 52 urges the drive shaft pin 32b of the drive shaft 32 to a proximal end of the first slot 42 of the carrier 28, thereby pulling the second arms 30b of respective pair of pivoting arms 30 towards each other, which in turn closes the breaking arms 114a, 114b towards each other. Accordingly, the breaking arms 114a, 114b are automatically returned to a closed position shown in FIG. 8 upon release of the button 46.

The retaining mechanism 112 includes a tab retaining pin 126. The tab retaining pin 126 is disposed within elongated slots 118a, 118b. A pin housing 126a in the form of a generally elongated slot transversing the width of the breaking arm 114a, 114b along the back wall 116f is included. The pin housing 126a is in open communication with a proximal end of the elongated slots 118a, 118b. The tab retaining pin 126 is movable between an engaged position and a disengaged position. In the engaged position the tab retaining pin 126 is displaced outwardly from the pin housing 126a so as to engage the tab 100 and hold the tab 100 by pinching the tab 100 between the tab retaining pin 126 and the inner ledges 116d, 116e of the elongated housing 116 as illustrated and discussed with respect to FIGS. 3-5. In the disengaged position the tab retaining pin 126 is moved up the elongated slots 118a, 118b and positioned within the pin housing 126a so as to be free of the tabs 100 as illustrated and discussed with respect to FIGS. 3-5.

The slide 120 may be provided with indicia to help instruct the user on how to release the tabs. The slide 120 is shown having a plurality of openings. It should be appreciated that the openings are provided for weight purposes and further help facilitate cleaning of the instrument 10.

Axial advancement of the drive shaft 32 pivots the breaking arms 114a, 114b. The breaking arms 114a, 114b are coupled to the drive shaft 32 by the pivoting arms 30. The first arm 30a of the pivoting arms 30 is rotatably mounted within the first slot 42 via the drive shaft pin 32b. The second arm 30b of the pivoting arm 30 is pivotably mounted to the pivot support structure 36 of respective breaking arms 114a, 114b.

The head portion 32c is mounted to the support head 38 of the carrier 28 and is prevented from advancing through the carrier 28 by an annular lip forming a distal end of the through hole 28a so as to work in concert with the first biasing member 24 to continuously urge the drive shaft 32 to the proximal end of the first slot 42. Thus, it should be appreciated that by actuating the button 46, the drive shaft 32 is displaced in the distal direction and the first arms 30a of the pivoting arms 30 are driven to the distal end of the first slot 42 of the carrier 28. Also, the second arms 30b are displaced outwardly from the carrier 28 which in turn radially displaces the breaking arms 114a, 114b away from each other. Specifically, the distal end of each breaking arm 114a, 114b is rotated about the indent 260 of respective first and second body portions 230, 240 of the reduction screw 200 and the tabs 100 are broken off from the body member 220 and held within respective breaking arms 114a, 114b.

In operation the user guides the instrument 110 so as to place a pair of tabs 100 into a respective elongated housing 116 between the back wall 116f and inner ledges 116d, 116e of the breaking arms 114a, 114b. The support head 38 of the carrier 28 is advanced forward until the support head 38 abuts against the polyaxial body of the reduction screw 200. The user simply pushes the button 46 which advances the drive shaft 32 towards the distal end of the carrier 28 and the breaking arms 114a, 114b pivot about the distal end of a carrier 28 and snap off the tabs 100 about their indents 260.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination.

The invention claimed is:

1. An instrument for breaking off and retaining at least one tab of a reduction screw, the instrument comprising:
    a breaking arm comprising a back wall, a pair of sidewalls extending from the back wall, and a pair of inner ledges spaced apart from the back wall extending from the pair of sidewalls along an axial length of the breaking arm and forming an elongated housing for receiving at least one tab of the reduction screw, the breaking arm configured to hold the at least one tab; and
    a retaining mechanism comprising a slide with a tab retaining pin and a biasing member configured to urge the tab retaining pin against the tab so as to retain a broken off tab within the elongated housing of the breaking arm.

2. The instrument as set forth in claim 1, a slide, wherein the slide is fixedly mounted to the tab retaining pin and operatively engaged with the biasing member.

3. The instrument as set forth in claim 2, wherein the slide is slidably mounted to the elongated housing.

4. The instrument as set forth in claim 3, wherein the elongated housing includes a block member, the biasing member disposed between the block member and the slide.

5. The instrument as set forth in claim 1, wherein the elongated housing includes a pin housing.

6. The instrument as set forth in claim 5, wherein the pin housing is generally a slot disposed on an inner surface of the back wall of the elongated housing and transversing a width of the breaking arm, wherein the pin housing is in open communication with a proximal end of the elongated slot.

7. The instrument as set forth in claim 6, wherein the slide includes a spring support fixedly mounted to the slide and the biasing member is disposed between the spring support and the block member.

8. The instrument as set forth in claim 1, further comprising a handle mounted to a proximal end of the breaking arm.

9. An instrument for breaking off and retaining at least one tab of a reduction screw, the instrument comprising:
    a pair of breaking arms, each of the pair of breaking arms comprising a back wall, a pair of sidewalls extending from the back wall, and a pair of inner ledges spaced apart from the back wall extending from the pair of sidewalls along an axial length of the breaking arm and forming an elongated housing for receiving at least one tab of the reduction screw;

a drive shaft;

a pair of pivot arms, each of the pair of pivot arms rotatably mounted to the drive shaft and a respective one of the pair of breaking arms, the drive shaft configured to advance axially between the pair of breaking arms so as to radially displace each of the pair of pivot arms away from each other and breaking the tab off of the reduction screw; and a retaining mechanism comprising a slide with a tab retaining pin and a biasing member configured to urge the tab retaining pin against the tab so as to retain a broken off tab within the elongated housing of each one of the pair of breaking arms.

10. The instrument as set forth in claim 9, further comprising a carrier configured to guide the drive shaft along an axis.

11. The instrument as set forth in claim 10, wherein the biasing member is operatively attached to the slide so as to urge the tab retaining pin to continuously engage the tab, wherein actuation of the slide disengages the tab retaining pin from the tab so as to release the tab from the respective breaking arm.

12. The instrument as set forth in claim 11, wherein the carrier includes a through hole, the drive shaft mounted within the through hole.

13. The instrument as set forth in claim 12, wherein the carrier includes a first slot, the first slot having a length extending along the length of the carrier, the drive shaft having a drive shaft pin extending radially from the drive shaft, the drive shaft pin disposed within the first slot.

14. The instrument as set forth in claim 13, further comprising a second biasing member and a head portion, wherein the second biasing member is disposed on a distal end of the drive shaft and urges the head portion distally so as to place the pair of breaking arms into a closed position.

15. The instrument as set forth in claim 9, wherein the elongated housing includes a pin housing.

16. The instrument as set forth in claim 15, wherein the pin housing is generally a slot disposed on an inner surface of the back wall and transversing a width of the breaking arm, wherein the pin housing is in open communication with a proximal end of the elongated slot.

17. An instrument for breaking off and retaining at least one tab of a reduction screw, the instrument comprising:

a back wall, a pair of sidewalls extending from the back wall, and a pair of inner ledges spaced apart from the back wall extending from the pair of sidewalls along an axial length of the breaking arm and forming an elongated housing for receiving at least one tab of the reduction screw;

a drive shaft;

a pair of pivot arms, each of the pair of pivot arms rotatably mounted to the drive shaft and a respective one of the pair of breaking arms, the drive shaft configured to advance axially between the pair of breaking arms so as to radially displace each of the pair of pivot arms away from each other and breaking the tab off of the reduction screw; and a retaining mechanism comprising a slide with a tab retaining pin, a first biasing member configured to urge the tab retaining pin against the tab so as to retain a broken off tab within the elongated housing of each one of the pair of breaking arms, a second biasing member and a head portion, wherein the second biasing member is disposed on a distal end of the drive shaft and urges the head portion distally so as to place the pair of breaking arms into a closed position.

18. The instrument as set forth in claim 17, wherein the pin housing is generally a slot disposed on an inner surface of the back wall and transversing a width of the breaking arm, wherein the pin housing is in open communication with a proximal end of the elongated slot.

* * * * *